United States Patent
Heppe

(10) Patent No.: US 10,952,635 B2
(45) Date of Patent: Mar. 23, 2021

(54) TEXTILE FABRIC FOR PLACING ON THE SKIN AND/OR A WOUND OF A PATIENT, AND TRANSDERMAL PATCH AND ARRANGEMENT CONSISTING OF A TRANSDERMAL PATCH AND AN EVALUATION UNIT

(71) Applicant: FRESENIUS MEDICAL CARE DEUTSCHLAND GMBH, Bad Homburg (DE)

(72) Inventor: John Heppe, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 281 days.

(21) Appl. No.: 15/557,595

(22) PCT Filed: Mar. 4, 2016

(86) PCT No.: PCT/EP2016/054708
§ 371 (c)(1),
(2) Date: Sep. 12, 2017

(87) PCT Pub. No.: WO2016/146410
PCT Pub. Date: Sep. 22, 2016

(65) Prior Publication Data
US 2018/0049667 A1 Feb. 22, 2018

(30) Foreign Application Priority Data
Mar. 16, 2015 (DE) .................. 10 2015 003 254.2

(51) Int. Cl.
*A61B 5/0537* (2021.01)
*D03D 1/00* (2006.01)
(Continued)

(52) U.S. Cl.
CPC ...... *A61B 5/0537* (2013.01); *A61F 13/00008* (2013.01); *A61F 13/00021* (2013.01);
(Continued)

(58) Field of Classification Search
CPC .. A61B 5/00; A61B 5/05; A61B 5/053; A61F 13/00; A61F 13/00029; A61F 13/00051;
(Continued)

(56) References Cited

U.S. PATENT DOCUMENTS

| 5,759,462 A * | 6/1998 | Jordan | B29C 55/023 264/105 |
| 6,183,770 B1 * | 2/2001 | Muchin | A61K 9/703 424/443 |

(Continued)

FOREIGN PATENT DOCUMENTS

| EP | 1997952 A2 | 12/2008 |
| WO | 2015022671 A1 | 2/2015 |

OTHER PUBLICATIONS

International Search Report and Written Opinion issued in corresponding International Patent Application No. PCT/EP2016/054708 dated May 31, 2016 (11 pages).
(Continued)

*Primary Examiner* — Daniel L Cerioni
*Assistant Examiner* — Raymond P Dulman
(74) *Attorney, Agent, or Firm* — Kilyk & Bowersox, P.L.L.C.

(57) ABSTRACT

A textile fabric is used to make a textile moisture sensor. The textile fabric has a top side facing away from the skin and/or a wound, and an underside that faces the skin and/or the wound and on which the textile fabric has a moisture-impermeable barrier. The textile fabric is formed from non-conductive warp threads, non-conductive weft threads, and conductive warp threads and/or conductive weft threads
(Continued)

that are arranged such that an electrically conductive structure is formed in the textile fabric. The moisture-impermeable barrier on the underside of the textile fabric has at least one opening and conductive warp and/or conductive weft threads arranged in the region of the opening such that the conductive threads can come into contact with moisture from the skin and/or wound in the region of the opening.

12 Claims, 2 Drawing Sheets

(51) Int. Cl.
    *D03D 15/00* (2021.01)
    *A61F 13/00* (2006.01)
    *A61F 13/42* (2006.01)
    *A61K 9/00* (2006.01)
    *D03D 11/00* (2006.01)
    *A61K 9/70* (2006.01)
    *D02G 3/44* (2006.01)
    *A61M 1/36* (2006.01)

(52) U.S. Cl.
    CPC ........ *A61F 13/00055* (2013.01); *A61F 13/42* (2013.01); *A61K 9/0009* (2013.01); *A61K 9/703* (2013.01); *A61K 9/7084* (2013.01); *A61M 1/3656* (2014.02); *D02G 3/441* (2013.01); *D03D 1/0088* (2013.01); *D03D 11/00* (2013.01); *D03D 15/00* (2013.01); *A61F 2013/424* (2013.01); *D10B 2401/16* (2013.01); *D10B 2509/022* (2013.01)

(58) Field of Classification Search
    CPC ......... A61F 2013/423; A61F 2013/424; D03D 15/00; D03D 1/0088; D02G 3/441; D10B 2401/00; D10B 2401/16; D10B 2401/18; A61K 9/7084; A61K 9/7092
    See application file for complete search history.

(56) References Cited

U.S. PATENT DOCUMENTS

| | | | |
|---|---|---|---|
| 6,283,938 B1 | 9/2001 | McConnell | |
| 7,295,867 B2* | 11/2007 | Berner | A61B 5/14532 600/345 |
| 9,439,599 B2* | 9/2016 | Thompson | A61B 5/0006 |
| 9,645,218 B2* | 5/2017 | Schroers | A61B 5/1495 |
| 2003/0211797 A1* | 11/2003 | Hill | H05K 1/038 442/205 |
| 2004/0030276 A1* | 2/2004 | Flick | A61F 13/00063 602/41 |
| 2007/0089800 A1* | 4/2007 | Sharma | D03D 1/0088 139/388 |
| 2008/0058703 A1* | 3/2008 | Subramony | A61K 9/0009 604/20 |
| 2011/0184257 A1* | 7/2011 | Boll | A61B 5/0002 600/306 |
| 2012/0190956 A1* | 7/2012 | Connolly | A61B 5/0537 600/372 |
| 2012/0191052 A1* | 7/2012 | Rao | A61M 5/142 604/290 |
| 2013/0053754 A1* | 2/2013 | Heppe | A61M 1/3653 604/6.16 |
| 2014/0012199 A1 | 1/2014 | Schroers et al. | |
| 2014/0039378 A1* | 2/2014 | Imran | A61N 1/0448 604/20 |
| 2014/0350502 A1* | 11/2014 | Berland | A61F 13/42 604/361 |
| 2015/0148735 A1* | 5/2015 | Friedrich | A61K 9/703 604/20 |
| 2016/0051416 A1* | 2/2016 | Vartiainen | A61F 13/42 156/256 |
| 2016/0166438 A1* | 6/2016 | Rovaniemi | A61F 13/00059 600/301 |
| 2017/0199143 A1* | 7/2017 | Nebuya | A61M 1/14 |
| 2017/0224280 A1* | 8/2017 | Bozkurt | G01L 5/0014 |

OTHER PUBLICATIONS

Notification of Transmission of Translation of the International Preliminary Report on Patentability dated Sep. 28, 2017 and International Preliminary Report on Patentability (Chapter I) issued in corresponding International Patent Application No. PCT/EP2016/054708 dated Sep. 19, 2017 (8 pages).

* cited by examiner

1 - 2 : $X_S$
1 - 3 : $X_L$
1 - 4 : $X_{LP}$
2 - 3 : $X_{LS}$
2 - 4 : $X_{LSP}$
3 - 4 : $X_P$

TEXTILE FABRIC FOR PLACING ON THE SKIN AND/OR A WOUND OF A PATIENT, AND TRANSDERMAL PATCH AND ARRANGEMENT CONSISTING OF A TRANSDERMAL PATCH AND AN EVALUATION UNIT

This application is a National Stage Application of PCT/EP2016/054708, filed Mar. 4, 2016, which claims priority to German Patent Application No. 10 2015 003 254.2, filed Mar. 16, 2015.

The invention relates to a textile fabric to be placed onto the skin and/or a wound of a patient, comprising a top side facing away from the skin and/or wound and an underside which faces the skin and/or wound and on which the textile fabric has a moisture-impermeable barrier, wherein the textile fabric is formed from non-conductive warp threads and non-conductive weft threads and from conductive warp threads and conductive weft threads which are arranged such that an electrically conductive structure consisting of conductive warp and/or weft threads is formed in the textile fabric. The invention also relates to a transdermal patch for applying an active substance, contained in an active substance reservoir, to the skin and/or wound of the patient, comprising a textile fabric of this type, and to an assembly consisting of a transdermal patch and an evaluation unit for detecting the amount of active substance in the active substance reservoir in the transdermal patch.

WO 2011/116943 discloses a moisture sensor intended for monitoring a vascular access and designed as a fabric made of non-conductive warp and weft threads and conductive warp and weft threads. The conductive warp and weft threads form an electrically conductive structure comprising connection lines having connection contacts for connecting to an evaluation unit. The evaluation unit measures the electrical resistance of the portion of the fabric located between the connection contacts. If liquid is added to the fabric, the electrical resistance thereof changes.

The textile moisture sensors are used to monitor an access to a patient which is used to supply a liquid to a patient and/or to remove a liquid from the patient via a hose line, in particular to monitor the vascular access in extracorporeal blood treatment. To monitor the vascular access, the textile moisture sensors are placed onto the patient's skin at the puncture site.

WO 2010/091852 describes a moisture sensor made of an absorbent material having an electrically conductive structure. The underside of the moisture sensor facing the patient's skin is completely covered with a liquid-impermeable barrier. This prevents moisture or perspiration from the patient's skin from reaching the electrically conductive structure.

Active substance patches which are bonded to the patient's skin are known for the application of an active substance. These active substance patches (also known as transdermal patches) comprise an active substance reservoir in which a particular amount of active substance is contained. To apply the active substance, the active substance patch has to be permeable to moisture in at least some portions of the underside thereof, yet this inevitably means that perspiration from the patient's skin can also enter the active substance patch.

The general problem addressed by the invention is that of providing a textile fabric which is to be placed onto the skin and/or a wound of a patient and allows moisture, in particular perspiration from the patient's skin, to be measured. Another object of the invention is to reduce the extent to which perspiration from the patient's skin affects a measurement result. In particular, the problem addressed by the invention is that of providing a transdermal patch that allows for the remaining amount of active substance in the active substance reservoir to be determined, the effect of perspiration from the patient's skin on the measurement result being reduced.

This problem is solved according to the invention by the features of claim 1. The dependent claims relate to advantageous embodiments of the invention.

The textile fabric according to the invention, which is to be placed onto the skin and/or a wound of a patient, is formed from non-conductive warp threads and non-conductive weft threads and from conductive warp threads and/or conductive weft threads which are arranged such that an electrically conductive structure consisting of conductive warp and/or weft threads is formed in the textile fabric. On the underside thereof, the textile fabric comprises a barrier which is impermeable to moisture and in which at least one opening is provided. Conductive warp and/or weft threads are arranged in the region of the at least one opening in the barrier. Since the conductive warp and/or weft threads come into contact with moisture from the patient's skin in the region of the opening, the conductive warp and/or weft threads can form an electrically conductive structure for measuring moisture. The moisture measurement makes it possible in particular to measure perspiration from the patient's skin.

In this connection, an opening is understood to be, for example, a punch-out, a clearing, a clearance, an orifice, a passage, a slot, a hole, a punch-hole, a recess, a gap or a perforation. The opening can be made by punching or cutting, in particular by means of a laser.

To place the textile fabric onto a wound, the opening has to be larger than the wound so that the textile fabric can stick to the skin surrounding the wound.

A preferred embodiment of the textile fabric provides that measured values are acquired using a first sensor and measured values are acquired using a second sensor, conductive warp and/or weft threads of the electrically conductive structure forming the first and second sensor. The electrically conductive warp and/or weft threads forming the first sensor are arranged in the region of a first opening in the moisture-impermeable barrier and the electrically conductive warp and/or weft threads forming the second sensor are arranged in the region of a second opening in the barrier. The first and/or second sensor can also only be formed from at least two warp threads or at least two weft threads in each case.

The first sensor and the second sensor can be designed differently and are used to acquire different measured variables. The sensors can be formed as resistive sensors, but can also be formed as capacitive sensors. The resistive sensors can be formed in each case by two warp threads or weft threads arranged at a spacing from one another, it being possible to measure the electrical resistance or the conductivity of the portion of the fabric between the adjacent warp or weft threads, respectively. The conductive warp and/or weft threads of the electrically conductive structure can also form the connection lines for the first and second sensors, it being possible for the ends of the connection lines of the first and second sensors to be formed as connection contacts, which are preferably provided on a portion of the textile fabric that is formed as a connection tab.

A preferred embodiment of the invention provides that one of the two sensors is a moisture sensor that allows moisture on the patient's skin to be measured, whilst the other sensor can be used to detect any given state or any given variable. The moisture measurement then makes it possible to compensate for the effect of moisture, in particular perspiration, on the patient's skin on the detection of the given state or the given variable.

A particularly preferred embodiment of the invention, in which the advantages of the invention are particularly effective, is the use of the textile fabric as a transdermal patch having an active substance reservoir, which contains a particular amount of an active substance which is applied over the skin or directly into the patient's wound when the transdermal patch is placed on the skin and/or wound. This embodiment allows the amount of active substance in the active substance reservoir to be determined, the effect of perspiration from the patient's skin on the measurement result being reduced.

The active substance reservoir is arranged in the region of the conductive warp and/or weft threads of the first sensor, which is arranged in the region of the first opening. The skin and/or wound of the patient comes into contact with the active substance through the first opening such that the active substance can be applied. The first sensor in the region of the opening comes into contact with both the active substance reservoir and perspiration from the skin. The second sensor is arranged in the region of the second opening, such that said second sensor can only come into contact with perspiration from the patient's skin.

To apply a sufficient amount of active substance, the first opening in the textile fabric preferably occupies a larger surface area than the second opening. The openings can be formed differently, for example rectangular, circular, etc. The shape of the opening for applying the active substance can be adapted to the size and shape of a wound or of a skin region to be supplied therewith.

If the main plane of extension of the first opening, provided for the active substance, in the moisture-impermeable barrier (first sensor) has a different surface area or is of a different size than the opening, provided for measuring perspiration, in the moisture-impermeable barrier (second sensor), a correction can be performed in the evaluation unit using a correction factor, and this can compensate for the effect of the different surface area or size of the first and second opening.

To detect the amount of active substance in the active substance reservoir in the active substance patch, the active substance patch according to the invention can be connected to an evaluation unit.

The evaluation unit according to the invention comprises an apparatus for acquiring the measured values from the first and second sensors, which apparatus is configured to obtain, from the measured values from the first sensor, a first measured value which correlates with both the amount of active substance in the active substance reservoir and moisture on the skin, and to obtain, from the measured values from the second sensor, a second measured value which correlates with moisture on the skin.

A preferred embodiment provides that the evaluation unit is configured to correct the first measured value using a correction value obtained from the second measured value. It is possible as a result to compensate for the effect that perspiration on the patient's skin has on the determination of the amount of active substance in the active substance reservoir.

The evaluation unit is preferably configured to generate a signal on the basis of the evaluation of the measured values from the first and second sensors, which signal indicates that there is still some active substance in the active substance reservoir, and/or to generate a signal which indicates that there is no more active substance in the active substance reservoir. These signals can be alarm signals which trigger an acoustic and/or optical and/or tactile alarm, or control signals which can be used to carry out actions in a machine control unit.

The measured values from the two sensors can be evaluated on the basis of various processes. In a preferred embodiment, the evaluation unit is configured to compare the first measured value with the second measured value, a signal being generated which indicates that there is no active substance in the active substance reservoir when the first measured value is the same as the second measured value or the difference between the first and second measured values is smaller than a predetermined limit value. In this case, the measured values from both sensors are at least approximately the same, since both sensors can only detect the perspiration from the skin. It is assumed in this case that the two openings are so close to one another that perspiration production in these regions is at least approximately the same.

A particularly preferred embodiment provides that the warp and/or weft threads of the electrically conductive structure are arranged such that four conductor track portions are arranged in the textile fabric at a spacing from one another, two conductor track portions being arranged at a spacing from one another in the region of the first opening and two conductor track portions being arranged at a spacing from one another in the region of the second opening. In each case, two conductor track portions formed from portions of the conductive threads form a measurement site (sensor). A connection line leads to each contact surface, connection contacts being formed at the ends of the connection lines. Furthermore, the warp and/or weft threads of the electrically conductive structure are arranged such as to form a connecting line interconnecting the first and third conductor track portions. In this embodiment, the evaluation unit comprises an apparatus which is configured to measure the electrical resistance between the first connection contact and the second connection contact, the electrical resistance between the first connection contact and the third connection contact, the electrical resistance between the first connection contact and the fourth connection contact, the electrical resistance between the second connection contact and the third connection contact, the electrical resistance between the second connection contact and the fourth connection contact, and the electrical resistance between the third and fourth connection contacts. By measuring these electrical resistances, the amount of active substance can be monitored independently of the production of perspiration, by using a suitable evaluation routine. It goes without saying that the conductivity can also be measured instead of the resistance.

An additional preferred use can be to compensate for the effect of perspiration on the monitoring of an access to a patient, which access is used to supply a liquid to a patient and/or to discharge a liquid from the patient via a hose line, in particular for monitoring the vascular access in extracorporeal blood treatment. In this embodiment of a textile fabric for monitoring a vascular access, the first sensor is a moisture sensor for measuring blood.

An embodiment of the invention will be explained in detail below with reference to the drawings, in which.

In the following, an embodiment is described for the use of the textile fabric according to the invention as a textile transdermal patch which has an active substance reservoir.

Figure 1:
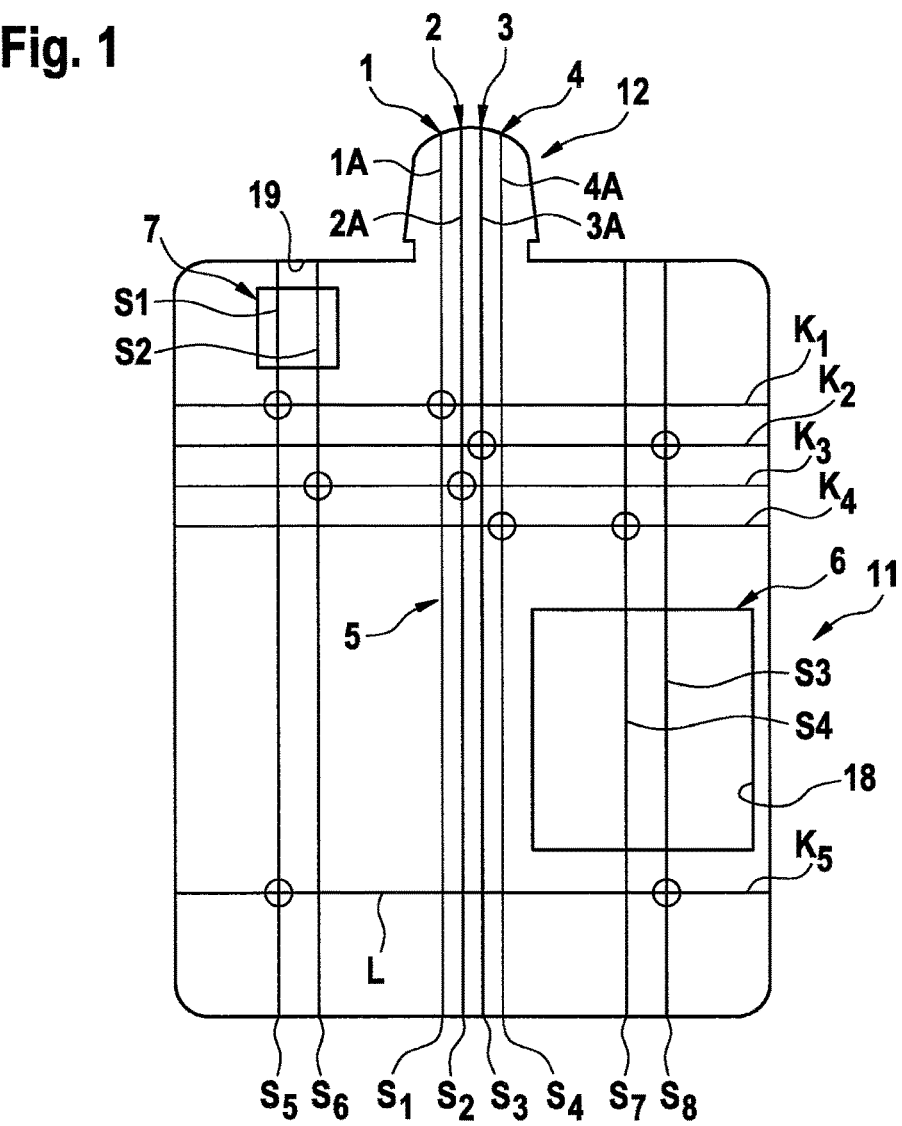
FIG. 1 is a simplified schematic view of a transdermal patch.
Figure 2:
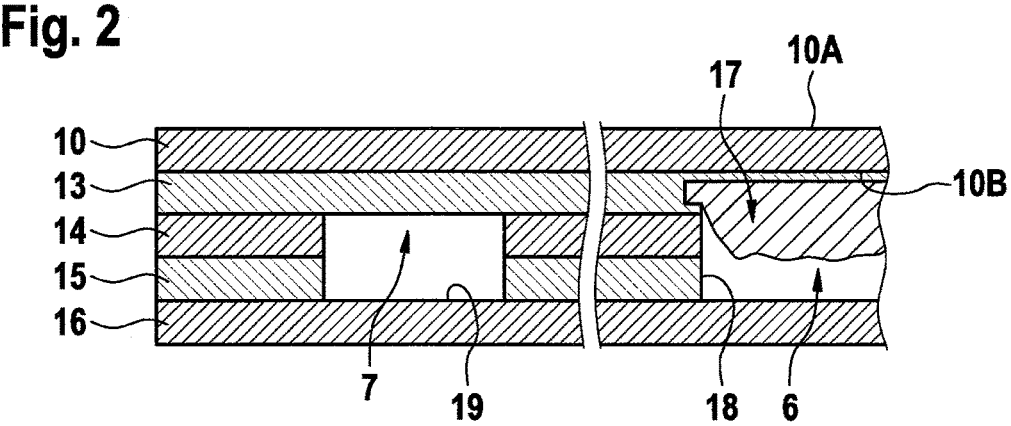
FIG. 2 is an enlarged cross section through the transdermal patch of FIG. 1.

FIG. 1 is a simplified schematic plan view of an embodiment of the active substance patch according to the invention. FIG. 2 is an enlarged cross section through the active substance patch.

The transdermal patch comprises a multilayer fabric 10, which is described in detail in WO 2011/116943. The multilayer fabric 10 consists of electrically conductive and electrically non-conductive warp and weft threads. The electrically conductive and electrically non-conductive warp and weft threads are arranged such that the fabric comprises a lower layer facing the patient's skin, a middle layer, and an upper layer facing away from the patient's skin. However, the separation of the fabric into a plurality of layers is merely used to aid understanding of the fabric structure, since the layers cannot be precisely separated from one another in practice. A structure of electrical conductor tracks is formed in the lower and middle layers of the fabric, in that the electrically conductive warp and/or weft threads are arranged at the intersection points such that they are either interconnected in an electrically conductive manner or are electrically insulated from one another. The upper layer of the fabric can be formed as an anti-contact insulation layer.

The active substance patch comprises a rectangular portion 11 having two longitudinal sides and two narrow sides. A connection tab 12 for connecting to an evaluation unit is preferably arranged in the centre of one of the two narrow or longitudinal sides. Two separate connection tabs can also be provided instead of one single connection tab, it being possible to establish an electrical connection between the first sensor (active substance) and the evaluation unit by means of one connection tab and to establish an electrical connection between the second sensor (perspiration) and the evaluation unit by means of the other connection tab.

The electrically conductive warp threads are denoted by "K" and the electrically conductive weft threads are denoted by "S". FIG. 1 does not show the electrically non-conductive warp and weft threads.

Four conductive weft threads S ($S_1$, $S_2$, $S_3$, $S_4$) lead from the connection tab 12 to the opposite side of the fabric, whilst on either side of the connection tab, two conductive weft threads S ($S_5$, $S_6$, $S_7$, $S_8$) each lead to the opposite side. On the half of the rectangular portion facing the connection tab 12, four conductive warp threads K ($K_1$, $K_2$, $K_3$, $K_4$) extend between the opposite sides, and one conductive warp thread K ($K_5$) extends on the half facing away from the connection tab. Circles mark the intersection points (contact points) of the conductive warp and weft threads K, S at which the warp and weft threads K, S are in electrical contact.

The ends of the conductive warp and weft threads K, S at the connection tab 12 are formed as connection contacts 1, 2, 3, 4, to which an electrical contact part (not shown in FIG. 1) of an evaluation unit can be connected.

The conductive warp and weft threads K, S form an electrically conductive structure 5 in the fabric 10. The warp and weft threads K, S are arranged in the fabric such that the electrically conductive structure 5 comprises a first resistive sensor 6 and a second resistive sensor 7, which are each formed by electrically conductive portions S3, S4 and S1, S2, respectively, of two parallel weft threads. In this case, each two adjacent conductive portions of the weft threads form electrical conductor track portions of a measurement site (sensor).

In a special alternative embodiment, the measurement sites each comprise one weft thread and one warp thread, which intersects said weft thread in the plan view of the fabric, the warp thread and the weft thread being insulated from each other at the intersection point in the three-dimensional fabric. When the intersection point gets wet, it becomes electrically conductive.

The fabric 10 consisting of non-conductive warp threads and non-conductive weft threads and conductive warp threads and conductive weft threads comprises a top side 10A facing away from the patient's skin. On the underside 10B facing the patient, the fabric is provided with an adhesive layer 13, on the underside of which there is a barrier 14 which is impermeable to liquid. The underside of the barrier is provided with an adhesive layer 15, to which a removable layer 16 adheres, for example a silicon film, which is removed prior to the active substance patch being applied to the patient's skin.

The fabric 10 comprises an active substance reservoir 17 (only shown indicatively) in which a particular amount of active substance is contained. A portion of the fabric is for example impregnated with the active substance.

In the barrier 14 provided with the adhesive layer 15, a first opening 18 is provided below the two parallel portions of the weft threads S3, S4 of the first resistive sensor 6, and a second opening 19 is provided below the two parallel portions of the weft threads S1, S2 of the second resistive sensor 7. The first opening 18 has a larger surface area than the second opening 19. The portion of the fabric having the active substance reservoir 17 is located above the first opening 18, so that once the silicon film 16 (also referred to as a liner) is removed, the active substance can come into contact with the skin and/or wound of the patient through the first opening 18.

The active substance reservoir 17 extends from the adhesive layer 13 into the opening 18 in the barrier 14, which is impermeable to liquid, and can touch the skin and/or wound of the patient when the silicon paper (liner) is removed and the patch is stuck to the patient's skin by the (thin) adhesive layer 15.

The electrical resistance of the portion of the fabric between the portions of the weft threads S3, S4 forming the first sensor 6 is dependent on the amount of active substance in the active substance reservoir 17. Therefore, measuring the resistance allows the amount of active substance in the reservoir to be monitored. The electrical resistance can, however, also be changed by perspiration, which can come into contact with the first sensor 6 through the opening 18. This can distort the measurement result. The active substance patch therefore provides the second sensor 7. The resistance of the portion of the fabric between the portions of the weft threads S1, S2 forming the second sensor 7 is dependent on the moisture on the patient's skin, i.e. the amount of perspiration that comes into contact with the second sensor 7 through the second opening 19. Since the active substance does not come into contact with the second sensor 7, the second sensor only measures the amount of perspiration on the skin, and this represents a correction value for the measured amount of active substance.

Figure 3:
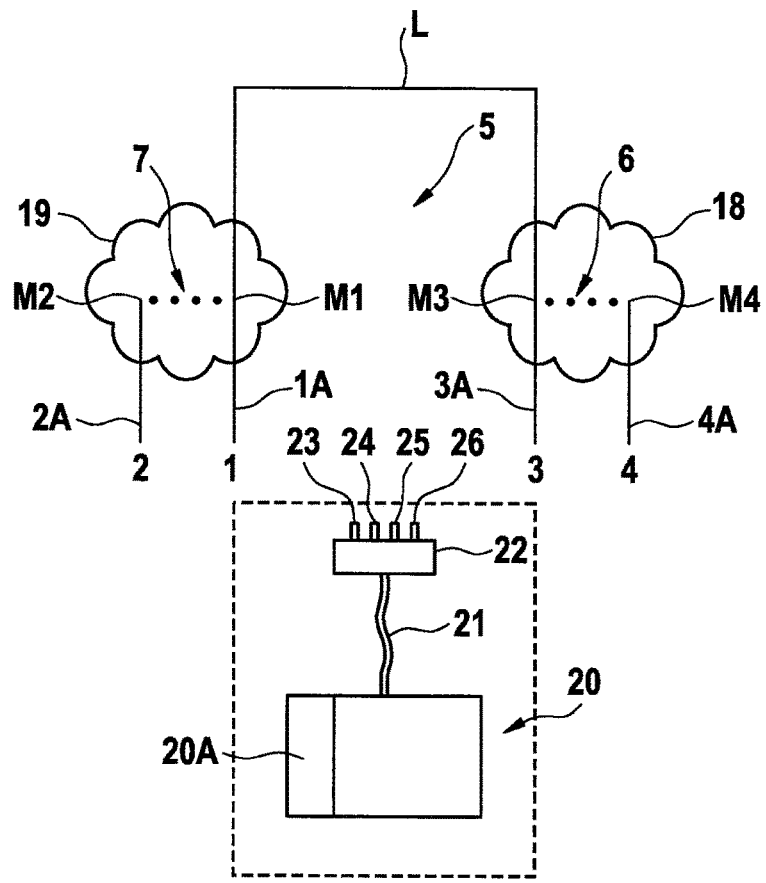
FIG. 3 is an equivalent electrical circuit diagram of the electrically conductive structure of the transdermal patch of FIG. 1.

FIG. 3 is an equivalent electrical circuit diagram of the electrically conductive structure 5 of the active substance patch shown in FIGS. 1 and 2. Like parts are provided with like reference numerals in the figures. The conductor track portions of the first sensor 6 and the conductor track portions of the second sensor 7, which are formed by the respective portions of the weft threads, are located at the points of contact with the patient's skin in the first and second openings 18, 19 in the barrier 14. A total of four conductor track portions M1, M2, M3, M4, which are arranged at a spacing from one another, are thus produced in the textile fabric, the third and fourth conductor track portions M3, M4 being arranged at a spacing from one another in the region of the first opening 18 and the first and second conductor track portions M1, M2 being arranged at a spacing from one another in the region of the second opening 19. The two conductor track portions in the first opening form the first sensor, whereas the two conductor track portions in the second opening form the second sensor. As a result, the sensors are formed from conductive portions of the warp and/or weft threads. The electrically conductive structure 5 further comprises a first connection line 1A leading to the first conductor track portion M1, a second connection line 2A leading to the second conductor track portion M2, a third connection line 3A leading to the third conductor track portion M3, a fourth connection line 4A leading to the fourth conductor track portion M4, and a connecting line L interconnecting the first and third conductor track portions M1, M3, the connection contacts 1, 2, 3, 4 being formed at the ends of the connection lines.

The resistance $x_P$ of the fabric between the conductor track portions M3 and M4, i.e. the measured value from the first sensor 6, is proportional to the amount of active substance and perspiration, whilst the resistance $x_S$ of the fabric between the conductor track portions M1 and M2, i.e. the measured value from the second sensor 7, is proportional to the amount of perspiration. The connecting line L has a resistance $x_L$. The resistance of the connection lines 1A to 4A is disregarded.

The resistance $x_S$ measured between the connection contacts 1 and 2 is dependent on the amount of perspiration, whilst the resistance $x_P$ measured between the connection contacts 3 and 4 is dependent on the amount of perspiration and the amount of active substance. The resistance $x_L$ of the connecting line L is measured between the connection contacts 1 and 3.

The resistance $x_{LP}$ measured between the connection contacts 1 and 4 is dependent on the resistance $x_L$ of the connecting line L and on the amount of perspiration and active substance, and the resistance $x_{LS}$ measured between the connection contacts 2 and 3 is dependent on the resistance $x_L$ of the connecting line L and on the amount of perspiration. The resistance $x_{LSP}$ measured between the connection contacts 2 and 4 is dependent on the resistance $x_L$ of the connecting line L and on the amount of perspiration and active substance.

If $x_P = x_S$, the conclusion can be drawn that the measured resistance can only be attributed to the perspiration, i.e. that all of the active substance in the active substance reservoir has been used. It can also be concluded that all the active substance has been used if $x_{LSP} = x_L + 2\ x_S$ or $x_{LSP} = x_L + 2\ x_P$ ($x_S = x_P$). If $x_{LSP} - x_L - 2x_S \neq 0$, however, the conclusion can be drawn that there is still some active substance in the active substance reservoir.

For one embodiment of a textile fabric, the following values are produced, by way of example, for the electrical resistances which are based on empirical values in known thread systems.

| | $x_S$ [Ω] |
|---|---|
| MIN | 100 (sample is wet) |
| DESIRED | 100000000 |
| MAX | 1000000000 (sample is dry) (variable) |

| | $x_L$ [Ω] |
|---|---|
| MIN | 30 |
| DESIRED | 60 |
| MAX | 100 (variable) |

| | $x_{LP}$ [Ω] |
|---|---|
| MIN | 130 |
| DESIRED | 100060 |
| MAX | 1000000100 (calculated value) |

| | $x_{LS}$ [Ω] |
|---|---|
| MIN | 130 |
| DESIRED | 100000060 |
| MAX | 1000000100 (calculated value) |

| | $x_{LSP}$ [Ω] |
|---|---|
| MIN | 230 |
| DESIRED | 100100060 |
| MAX | 2000000100 (calculated value) |

| | $x_P$ [Ω] |
|---|---|
| MIN | 100 |
| DESIRED | 100000 |
| MAX | 1000000000 |

Figure 4:
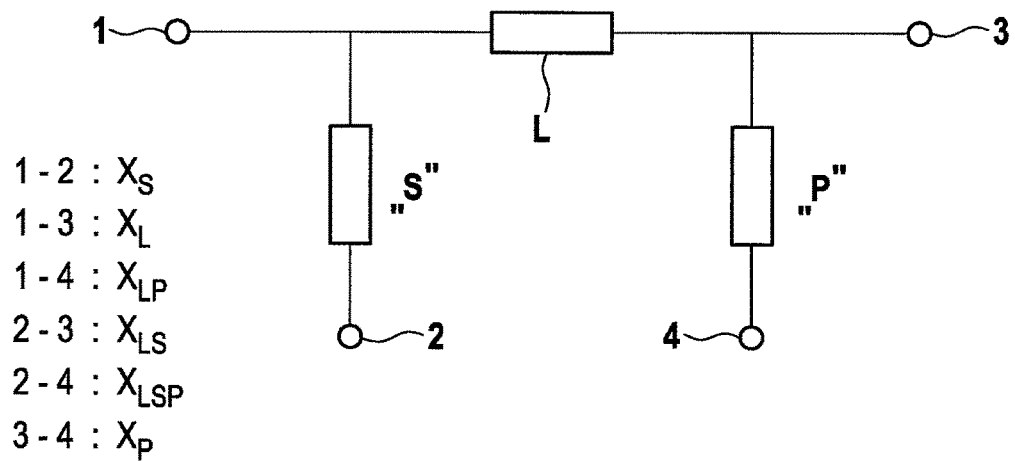
FIG. 4 is an equivalent electrical circuit diagram for one embodiment.

FIG. 4 is an equivalent electrical circuit diagram for the embodiment having the resistances "S" (perspiration) and "P" (active substance) and L (connecting line).

For evaluating the measurement results, provision is made of an evaluation unit 20 which comprises a connection cable 21 having a connecting part 22 which has four connection contacts 23, 24, 25, 26 connected to the connection contacts 1, 2, 3, 4 of the connection tab 12 of the active substance patch (FIG. 3). The evaluation unit 20 comprises an apparatus which is configured to measure the electrical resistance $x_S$ between the first connection contact 1 and the second connection contact 2, the electrical resistance $x_L$ between the first connection contact 1 and the third connection contact 3, the electrical resistance $x_{LP}$ between the first connection contact 1 and the fourth connection contact 4, the electrical resistance $x_{LS}$ between the second connection contact 2 and the third connection contact 3, the electrical resistance $x_{LSP}$ between the second connection contact 2 and the fourth connection contact 4, and the electrical resistance $x_P$ between the third and fourth connection contacts 3, 4.

In one embodiment, the evaluation unit 20 is configured to compare the difference $x_P - x_S$ with a predetermined limit value, which can also be zero ($x_P = x_S$). If the difference $x_P - x_S$ is greater than or equal to the limit value, the evaluation unit 20 generates a signal indicating that there is still a sufficient amount of active substance in the active substance reservoir. If the difference $x_P - x_S$ is less than the limit value, however, the evaluation unit 20 generates a signal indicating that there is no active substance left in the active substance reservoir. If $x_{LSP} - x_L - 2\ x_S \neq 0$, the evaluation unit 20 generates a signal indicating that there is still some active substance in the active substance reservoir.

An alternative embodiment provides that the absolute amount of active substance is measured using a correction of the measured values. In this embodiment, a function describing the dependence of the resistance measured using the first sensor 6 on the amount of active substance is stored in a memory 20A in the evaluation unit 20. This function can be determined during tests. The evaluation unit 20 is configured to calculate a value for the amount of active substance from the resistance value measured using the first sensor. At the same time, the second sensor 7 measures a value for the amount of perspiration, an empirically determined function also being stored for the dependence of the resistance on the amount of perspiration. In addition, a correction function is stored in the memory 20A in the evaluation unit 20, and this can be used to correct the previously calculated value for the amount of active substance on the basis of the measured amount of perspiration. As a result, it is possible to determine an exact value for the amount of active substance, which value is not affected by the perspiration. The correction function can be determined during tests.

The invention claimed is:

1. A device comprising a transdermal patch for applying an active substance to a skin and/or a wound of a patient, and an evaluation unit, the transdermal patch comprising a textile fabric and an active substance reservoir, the textile fabric comprising a top side facing away from the skin and/or wound and an underside that faces the skin and/or wound and on which the textile fabric has a moisture-impermeable barrier, an adhesive layer provided on an underside of the moisture-impermeable barrier, and a removeable liner adhered to the adhesive layer, the textile fabric being formed from non-conductive warp threads and non-conductive weft threads and from conductive warp threads and/or conductive weft threads that are arranged such that an electrically conductive structure consisting of conductive warp and/or weft threads is formed in the textile fabric, wherein
   at least two openings are defined through the moisture-impermeable barrier and the adhesive layer, below the conductive warp and/or conductive weft threads, the conductive warp and/or conductive weft threads being arranged in a first region of a first opening of the at least two openings and being arranged in a second region of a second opening of the at least two openings such that the conductive warp and/or conductive weft threads can come into contact with moisture from the patient's skin and/or wound in the first region and the second region,
   the conductive warp and/or conductive weft threads form a first sensor and the conductive warp and/or conductive weft threads form a second sensor, the conductive warp and/or conductive weft threads that form the first sensor being arranged in the first region of the first opening of the at least two openings, and the conductive warp and/or conductive weft threads that form the second sensor are arranged in the second region of the second opening of the at least two openings,
   the active substance reservoir is arranged in the first region of the conductive warp and/or conductive weft threads of the first sensor, which is arranged in the first region of the first opening, such that the first sensor can come into contact with both the active substance reservoir and moisture from the skin,
   the evaluation unit is configured to detect an amount of active substance in the active substance reservoir and comprises a memory and a connection cable having a connecting part,
   the connecting part has four connection contacts,
   the evaluation unit comprises an apparatus for acquiring measured values from the first sensor and for acquiring measured values from the second sensor,
   the apparatus is configured to obtain, from the measured values from the first sensor, a first measured value that correlates with the amount of active substance in the active substance reservoir and with moisture on the skin and/or the wound, and to obtain, from the measured values from the second sensor, a second measured value that correlates with the moisture on the skin and/or the wound, and
   the apparatus is also configured to measure electrical resistance between the connection contacts.

2. The device according to claim 1, wherein the first sensor and the second sensor are formed as resistive sensors.

3. The device according to claim 1, wherein the first sensor and the second sensor are formed in each case by two warp threads or weft threads that are arranged at a spacing from one another.

4. The device according to claim 1, wherein conductive warp and/or conductive weft threads form connection lines for the first sensor and conductive warp and/or conductive weft threads form connection lines for the second sensor.

5. The device according to claim 4, wherein ends of the connection lines of the first sensor are formed as a first set of connection contacts and ends of the connection lines of the second sensor are formed as a second set of connection contacts.

6. The device according to claim 5, wherein a portion of the textile fabric is formed as a connection tab, on which at least one of the first set of the connection contacts or the second set of connection contacts are arranged.

7. The device according to claim 1, wherein the first opening in the textile fabric occupies a larger surface area than the second opening.

8. The device according to claim 1, wherein the evaluation unit is configured to correct the first measured value using a correction value obtained from the second measured value.

9. The device according to claim 1, wherein the evaluation unit is configured to generate a signal on the basis of an evaluation of the measured values from the first and second sensors, which signal indicates that there is active substance in the active substance reservoir, and/or to generate a signal that indicates that there is no active substance in the active substance reservoir.

10. The device according to claim 8, wherein the evaluation unit is configured to compare the first measured value with the second measured value, and to generate a signal that indicates that there is no active substance in the active substance reservoir when the first measured value is the same as the second measured value or when the difference between the first and second measured values is smaller than a predetermined limit value.

11. The device according to claim 9, wherein
   the warp and/or weft threads of the electrically conductive structure are arranged such that four electric conductor track portions are arranged in the textile fabric at a spacing from one another, two conductor track portions of the four being arranged at a spacing from one another in the region of the first opening and forming the first sensor, and two conductor track portions of the four being arranged at a spacing from one another in the region of the second opening and forming the second sensor, and
   a first connection line is formed leading to a first conductor track portion of the four, a second connection line is formed leading to a second conductor track portion of the four, a third connection line is formed leading to a third conductor track portion of the four, a fourth connection line is formed leading to a fourth conductor track portion of the four, and a connecting line is formed interconnecting the first and third conductor track portions, first, second, third, and fourth connection contacts are formed at the ends of the first, second, third, and fourth connection lines, respectively, and the evaluation unit comprises the apparatus and the apparatus is configured to measure the electrical resistance between the first connection contact and the second connection contact, the electrical resistance between the first connection contact and the third connection contact, the electrical resistance between the first connection contact and the fourth connection contact, the electrical resistance between the second connection contact and the third connection contact, the electrical resistance between the second connection contact and the fourth connection contact, and the electrical resistance between the third connection contact and the fourth connection contact.

12. A method comprising:

providing the device according to claim 1; and removing the removeable liner from the adhesive layer.

* * * * *